US010946379B2

(12) United States Patent
Smith et al.

(10) Patent No.: US 10,946,379 B2
(45) Date of Patent: Mar. 16, 2021

(54) MICROFLUIDICS SYSTEM

(71) Applicant: HEWLETT-PACKARD DEVELOPMENT COMPANY, L.P., Houston, TX (US)

(72) Inventors: Matthew David Smith, Corvallis, OR (US); Manish Giri, Corvallis, OR (US); Chantelle Domingue, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 316 days.

(21) Appl. No.: 15/748,535

(22) PCT Filed: Jan. 29, 2016

(86) PCT No.: PCT/US2016/015622
§ 371 (c)(1),
(2) Date: Jan. 29, 2018

(87) PCT Pub. No.: WO2017/131736
PCT Pub. Date: Aug. 3, 2017

(65) Prior Publication Data
US 2018/0214867 A1 Aug. 2, 2018

(51) Int. Cl.
B01L 3/00 (2006.01)
C12M 3/06 (2006.01)
(Continued)

(52) U.S. Cl.
CPC ......... B01L 3/50273 (2013.01); C12M 23/16 (2013.01); G16H 40/63 (2018.01);
(Continued)

(58) Field of Classification Search
CPC ......... B01L 3/50273; B01L 2300/0864; B01L 2300/0867; B01L 2300/0627;
(Continued)

(56) References Cited

U.S. PATENT DOCUMENTS 5,347,864 A 9/1994 Senghaas et al.
6,126,899 A 10/2000 Woudenberg et al.
(Continued)

FOREIGN PATENT DOCUMENTS

CN 103003577 A 3/2013
EP 0816081 A2 1/1998
(Continued)

OTHER PUBLICATIONS

Moon, Hyejin, et al. "An integrated digital microfluidic chip for multiplexed proteomic sample preparation and analysis by MALDI-MS", Lab Chip, 2006, 6, 1213-1219.

Primary Examiner — Samuel P Siefke
Assistant Examiner — Quocan B Vo
(74) Attorney, Agent, or Firm — Fabian VanCott

(57) ABSTRACT

Provided herein are a system and method for using a microfluidics device. The system includes: a plurality of pumps and a plurality of sensors; a first communication line to select a pump from the plurality of pumps and select a sensor from the plurality of sensors; a second communication line selectively connected to the selected pump; and a third communication line selectively connected to the selected sensor.

14 Claims, 5 Drawing Sheets

(51) Int. Cl.
*G16H 40/63* (2018.01)
*G16H 50/20* (2018.01)
*G11C 19/28* (2006.01)

(52) U.S. Cl.
CPC ...... *G16H 50/20* (2018.01); *B01L 2300/0627* (2013.01); *B01L 2300/0864* (2013.01); *B01L 2300/0867* (2013.01); *B01L 2400/0442* (2013.01); *G11C 19/28* (2013.01)

(58) Field of Classification Search
CPC ........... B01L 2400/0442; C12M 23/16; G16H 40/63; G16H 50/20; G11C 19/28
See application file for complete search history.

(56) References Cited

U.S. PATENT DOCUMENTS

| | | | |
|---|---|---|---|
| 6,529,546 | B2 | 3/2003 | Schilling |
| 8,692,298 | B2 | 4/2014 | Rothberg et al. |
| 8,721,892 | B2 | 5/2014 | Shih et al. |
| 2001/0026935 | A1 | 10/2001 | Ackley |
| 2001/0052460 | A1 | 12/2001 | Chien et al. |
| 2005/0152808 | A1 | 7/2005 | Karthik |
| 2005/0259778 | A1* | 11/2005 | Kimura ................... G11C 19/00 377/78 |
| 2007/0225675 | A1 | 9/2007 | Robinson et al. |
| 2009/0257886 | A1 | 10/2009 | Rosenstein et al. |
| 2011/0033315 | A1 | 2/2011 | Gridelet |
| 2013/0015877 | A1 | 1/2013 | Jie |
| 2013/0027075 | A1 | 1/2013 | Shao |
| 2018/0302076 | A1* | 10/2018 | Fujita ..................... H03M 9/00 |

FOREIGN PATENT DOCUMENTS

| | | |
|---|---|---|
| EP | 0908955 A1 | 4/1999 |
| EP | 2921919 | 9/2015 |
| WO | WO-2011017077 | 2/2011 |
| WO | PCT/US2015/013881 | 8/2016 |

\* cited by examiner

MICROFLUIDICS SYSTEM

BACKGROUND

Microfluidics test methods are seeing increasing development to provide point of care (POC) testing. Point of care focuses on providing diagnostic or other testing services at the site of sample collection. For medical testing, this allows the test results to be provided while the medical personnel and the patient are still together, avoiding a second visit and allowing immediate commencement of appropriate treatment. It avoids the delay in waiting for test results or the risk of beginning the potentially wrong treatment in the absence of a diagnosis.

BRIEF DESCRIPTION OF THE DRAWINGS

The accompanying drawings illustrate various examples of the principles described herein and are a part of the specification. The illustrated examples are intended to describe examples and do not limit the scope of the claims. Like numerals denote similar but not necessarily identical elements.

DETAILED DESCRIPTION

Figure 1:
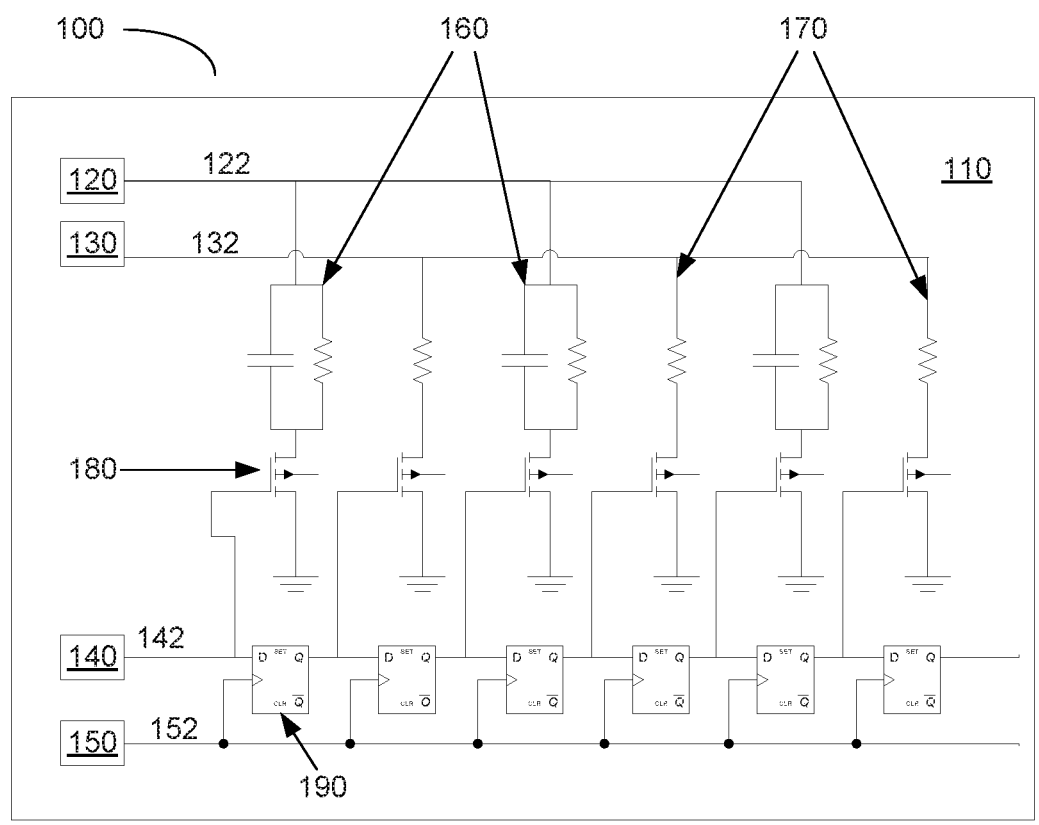
FIG. 1 shows an example system consistent with this specification.

Point of care tests face additional demands over lab based tests. In POC testing, components may need to be shelf stable. In contrast, labs may use reagents that use refrigeration, freezing, or other special storage conditions. POC testing equipment may need to be portable. In contrast, lab equipment may be larger. Ideally, the testing is available to the same number of patients, which in turn, implies more testing devices compared with a single lab setup. Testing procedures may need to be simplified to allow patient contacting medical professionals to reliably and reproducibly obtain results. In contrast, labs often employ specialists to perform testing.

One advantage POC tests have is that there is often a short time between sample acquisition and testing. This may avoid the need for specialized handling and shipping procedures (e.g. ice packs) to avoid sample degradation. POC samples also may be less vulnerable to contamination or mix-up during handling because the sample may be acquired and processed by the same individual without other samples in the vicinity. However, despite these advantages, the technical and economic advantages of traditional lab base approaches represent a significant challenge to new POC tests.

Accordingly, development of POC devices and test methods focuses on developing reliable, robust tests performable at reasonable cost at the point of care. In the end, increased cost of the POC method over a lab-based test balances against the benefit of the medical benefits of reduced time for the medical provider to obtain results.

Microfluidics testing generally refers to performing testing on small volumes of fluid, generally in the nanoliter (nl) to picoliter (pl) range. The test sample is often extracted from a larger sample, for example in the microliter ($\mu$l) or milliliter (ml) range. For medical tests, small samples can often be acquired with less pain and/or injury to a patient. The small sample volumes also allow multiple tests to be performed on a single sample. In some cases, these include different kinds of tests performed simultaneously or sequentially on a microfluidics device. In other cases, they include replicates, including true replicates and time series replicates. The small size of the hardware involved often makes it practical to perform replicate measurements without additional material or time cost. This can improve the reliability of the test by averaging the results of multiple runs. As discussed below, the methods described in this specification may facilitate performing multiple tests using a single chip and/or cartridge without significant impacting the chip/cartridge cost.

While a variety of different models exist for performing microfluidics tests, one model may offer some advantages. In this model, the test system is divided into two components, the device and the cartridge. The device is a reusable component that is used for multiple tests. Often times the device is larger than the cartridge. The device may include a processor and other electronic components to control and regulate the activities on the cartridge. The device may include a memory and communication ports or systems. In some examples, the device is handheld. In most examples, the device is compact and portable. The device may be considered a durable medical device.

The cartridge is a component used to support or enable the device to perform the desired test. The device may support many kinds of cartridges or a single type. The cartridge is often disposable. However, cartridges can be recycled, refurbished, reconditioned, and/or reloaded depending on the economics and healthcare safety of reuse vs. make new. The cartridge interfaces with the device. While this often takes the form of a physical connection with electrical contacts, it can also be performed using a wireless connection, such as Bluetooth, WI-Fi, or other local communication method. The goal of the cartridge is to reduce the costs of the cartridge while enabling the cartridge to enable the desired microfluidics method. This lowers the per test cost. Accordingly, the cartridge may have a minimal number of electronics components, especially when those functions can be provided by the device. In contrast, the cartridge generally does contain the materials to perform the specific test, for example, reagents, or other materials rather than attempting to move such materials from the device to the cartridge as part of the testing process.

While a cartridge can take a variety of different physical forms, the development of precision electronics manufacturing techniques and the associated field of microelectromechanical systems (MEMS) has provided tools to support relatively low cost, high volume, precision micro-manufacturing. Accordingly, many cartridges include MEMS as the 'guts' of the cartridge. The cartridge may include additional components, including reservoirs, batteries, and electronic components that are more difficult or uneconomical to form using MEMS fabrication techniques. The MEMS may be built up on a substrate and while silicon wafers and similar semiconductor substrates are available, a wide variety of substrates may be used.

Accordingly, the present specification describes, among other examples, a microfluidics system. The system comprising: a plurality of pumps and a plurality of sensors; a first communication line to select a pump from the plurality of pumps and select a sensor from the plurality of sensors; a second communication line selectively connected to the selected pump; and a third communication line selectively connected to the selected sensor.

The present specification also describes a method of making microfluidics measurements. The method comprising: using a single communication line, selecting a sensor from a plurality of sensors and a pump from a plurality of pumps; activating the selected pump; and obtaining a sensor measurement from the selected sensor during the activation of the selected pump.

The present specification also describes a microfluidic measurement system. The microfluidics measurement system comprising: a substrate; a plurality of transistors mounted on the substrate; a plurality of pumps mounted on the substrate, each pump having an associated transistor, wherein a state of an associated transistor controls whether a corresponding pump is selected; a plurality of sensors mounted on the substrate, each sensor having an associated transistor, wherein a state of an associated transistor determines whether a corresponding sensor is selected; a series of flip-flops, where each transistor of the plurality of transistors has an associated flip-flip that controls a state of the corresponding transistor; a data line providing a state to a first flip-flop in the series of flip-flops; a pump activation line selectively connected electrically to a selected pump; a sensor line selectively connected electrically to the selected sensor; and a signal line to provide a signal to the series of flip-flops, upon receipt of the signal on the signal line, a state of a flip-flop in the series of flip-flops is transmitted to a next flip-flop in the series of flip-flops.

Turning now to the figures:

FIG. 1 shows a system consistent with this specification. The system (100) includes a substrate (110) with a plurality of pumps (170) and a plurality of sensors (160). While any number of pumps (170) and sensor (160) can be produced on the substrate (110), a finite number are shown in the figures for clarity. The system (100) includes a number of communication lines that allow the components on the substrate to send and receive signals from an external source. The communication lines connect to pads (120, 130, 140, 150) which provide the contacts to external components. Each pump (170) and each sensor (160) has a transistor (180) associated with it. When the transistor (180) is in a first state, the associated pump (170) and/or sensor (160) is connected with an external communication pad (120, 130). When the transistor is in a second state, the associated pump (170) and/or sensor (160) is not connected with an external communication pad (120, 130). The transistors (180) are controlled by a series of flip-flops (190) so that each time a signal is provided to the system by a signal pad (150), the values in the transistors (180) are propagated to the next transistor (180) in the chain. Accordingly, the whole of a chain of X transistor can be set to the proper states by providing the proper sequence of states on a data pad (140) and advancing the states down the chain of flip-flops (190) and associated transistors (180) by applying a series of signals on the signal pad (150).

The line associated with the first external communication pad (120) is the pump activation line (122). The line associated with the second external communication pad (130) is the sensor line (132). The line associated with the data pad (140) is the data line (142). The line associated with the signal pad (150) is the signal line (152).

One advantage of this approach is it limits the number of pads needed to manage any number of pumps (170) and/or sensors (160). This reduces the cost of fabricating the system (100), which in turn reduces the per test cost.

One examples uses a single external communication pad (120, 130) and associated line to both provide the firing impulses to the pumps (170) and obtain measurements from the sensors (160). However, this design has some challenges. Specifically, for some types of testing, the firing pulses applied through created significant noise on the shared communication line and associated external communication pad (120, 130). Further, sensor measurements are not available while using the shared communication line to activate the pump. Also, in this example there is a time lag during shifting the communication line from a pump (170) to a sensor (160) during which measurements are not obtained. Similarly, when a sequence of pumping and measurements were needed, the system had gaps in the measurement windows when pumping and shifting between measurement and pumping.

In contrast, the present system, with its independent communication pads for the pumps (130) and the sensors (120) allows a sensor to measure while a pump is active. This separation also isolates the two signals, preventing inadvertent application of relatively large pump voltages to the sensors. This approach reduces cross talk between the pump firing signals and the sensor output, which improves the signal to noise ratio (S/N ratio) for the sensor measurements. Improved S/N ratio can allow the use of less expensive components to obtain similar measurements and/or can be used to improve the quality of the measurements depending on the specific design goals for the device.

The system (100) is a system for preforming microfluidics measurements. It includes a variety of components mounted on a substrate (110). The system (100) may be designed to interact with a separate device. In some examples, the system is a cartridge (100). In some examples, the system is disposable. In other examples, the system is reusable and/or refurbishable.

The substrate (110) supports the components of the system (100). In some examples, the substrate (110) comprises silicon. The substrate (110) may include internal conductive traces and/or components. Other conductive traces and/or components may be mounted on one or both surfaces. The substrate includes a number of pads (120, 130, 140, 150) for facilitating communications off the substrate (110). The pads (120, 130, 140, 150) may make electrical connection with external conductors. The pads (120, 130, 140, 150) may communicate wirelessly, optically, by radio, electromagnetic wave, and/or similar technologies. In one example, the substrate (110) includes a power source such as a battery that converts the signals received at the pads into electrical signals. In other examples, power is provided by an external device by a direct connection and/or inductive transfer.

The first external communication pad (120) provides firing pulses to the pumps (170) on the substrate (110). The firing pulses travel from the first external communication pad (120) to the pumps (170) that have a selected associated transistor (180). The firing pulses are prevented from traveling to the pumps (170) that do not have a selected associated transistor (180). In one example, a single pump (170) is selected at a time. In other examples, multiple pumps (170) may be selected and fired at the same time. A pump (170) may be activated while a measurement is being acquired from a sensor (160). Alternately, a pump (170) may perform fluid handling before and/or after sensor (160) measurements. The pumps (170) may be any suitable pump (170) sized to operate with the substrate (110). The pumps (170) may be a piezoelectric membrane pumps (170). The pumps (170) may be bubble pumps (170) which operate by vaporizing a portion of a fluid to produce an expanding bubble. The pumps (170) may include associated valves, including one-way valves. The pumps (170) need not be the same type or design, although there are manufacturing advantages to standardizing them. The pumps (170) may be augmented with evaporative and/or capillary actions to facilitate fluid management on the substrate (110).

The second external communication pad (130) is used to provide sensor measurements to an external location. This external location may be a device. The external location may be the source of the firing pulses. The external communication pad is connected to a single sensor (160) using a selected transistor (180). Incrementing or loading new bits into the flip-flops (190) allows the selected transistor (180) to be changed to a different transistor (180) associated with a different sensor (160). The second communication pad (130) is not connected with multiple sensors (160) simultaneously. If measurements are desired to be made on two different sensors (160) simultaneously, a third external communication pad (not show) can be incorporated into the system (110) and some of the sensors (160) are made to communicate through the second external communication pad (130) and some sensors are made to communicate through the third external communication pad. This approach can be repeated to add even more sensors available for simultaneous measurement. However, there are diminishing returns as each sensor (160) that can be simultaneously measured adds an additional external communication pad (120, 130) with the associated monetary and equipment cost.

The data pad (140) provides the bits that are loaded into the flip-flops (190). Those bits determine the states of the transistors (180). The transistors (180), in turn, control which sensor (160) and pump(s) (170) are available on the external communication pads (120, 130).

The signal pad (150) provides signals to the flip-flops (190) to advance the stored bit to the next flip-flop (190) in the chain. These stored bits, in turn, control the state of the transistors (180) which in turn control which sensor (160) and pump(s) (170) are available on the external communication pads (120, 130). The signal can be any suitable signal. In one example, the signal is a clock signal. In one example, the signal is a level signal. In another example, the signal is an edge signal.

The sensors (160) can include any of a variety of sensors that may be used to make measurements in a microfluidics environment. The sensors (160) may be all of the same type. Alternately, the sensors (160) may include a variety of different sensors types. The sensors (160) are likely located at different positions on the substrate (110). The material being evaluated by the sensors (160) may be subjected to a variety of preloading or on substrate processing prior to taking the sensor (160) measurement. Detailed description of the particular sensor (160) types and their method of operation is not the purpose of this specification. However, a non-limiting list of examples of sensors and measurements includes: impedance sensors, absorbance sensors, optical sensors, proximity sensors, composition sensors, ultrasound sensors, capacitive sensors, and resonance sensors. As discussed above, a single sensor is electrically available at the second external communication pad (130) at a given time. To make a multiple sensors available simultaneously, an additional external communication pad can be added and indexed with the flip-flops (190) and transistors (180).

The pumps (170) facilitate fluid management. The pumps (170) may be any suitable pump (170) that can operate with the substrate (110). The pumps (170) may be piezoelectric membrane pumps (170). The pumps (170) may be bubble pumps (170) which operate by vaporizing a portion of a fluid to produce an expanding bubble. The pumps (170) may include associated valves, including one-way valves. The pumps (170) need not be the same type or design, although there are manufacturing advantages to standardizing them. The pumps (170) may be augmented with evaporative and/or capillary actions to facilitate fluid management on the substrate (110). A pump (170) is associated with the first external communication pad (120) using the transistors (180) and the flip-flops (190). In some examples, multiple pumps (120) may be associated with the first external communication pad (120) at the same time.

The transistors (180) perform the selection of the addressable sensor (160) and pump (170). The transistor (180) state is controlled by an associated flip-flop (190). Bits are loaded into the flip-flops (190) using the data pad (140) and the signal pad (150). Those bits are propagated down the chain of flip-flops (190). This approach allows the selection from a large number of sensors using two pads (140, 150). Accordingly, the system can include a larger number of different sensor geometries, pump types, configurations, etc. without increasing the number of pads and the associated costs. This provides greater flexibility in design and allows a given system (100) design to provide a larger number of tests. Using a single design to support more tests, in turn, reduces the number of systems (100) that need to be available. It also facilitates economies of scale in both manufacturing and supply management.

The flip-flops (190) allow the bits that control the transistors (180) to be provided to the system (100) via serial action using the data pad (140) and signal pad (150). The flip-flops (190) are chained together so that with each appropriate signal on the signal pad (150), the bits advance to the next flip-flop (190). This in turn allows the state of the transistors (180) to be controlled, which in turn provides selection of the pump (170) and/or sensor (160) in communication with the external communication pads (120, 130). The use of the serial communication allows the data pad (140) and signal pad (150) to select from any number of pumps (170) and/or sensors (160). In contrast, using parallel communication uses log 2 (n) pads.

The term flip-flops (190) as used in this specification and the associated claims includes both edge sensitive and level sensitive devices. Accordingly, it also includes latches including simple latches and similar devices that are capable of maintaining two distinct states and propagating those states down the series of devices in response to an input. While the input may be provided as a clock signal, any suitable triggering input will provide the same functionality. Alternately, the input may be a level, transition, edge, etc.

FIG. 1 shows the use of single data line to load the flip-flops (190). However, other configurations are possible. For example, if the loading or switching time is unacceptably long, additional data pads can be provided and the flip-flops (190) divided into banks. In one example, the transistors (180) that control selection of the pumps (170) are in a first bank and the transistors (180) that control selection of the sensors (160) are in a second bank. In another example, each bank includes transistors that control both pumps (170) and/or sensors (160). Clearly, additional banks of flip-flops (190) can be added to optimize the tradeoff between cartridge cost and loading speed.

FIG. 1 also shows that the state of the first transistor (180) is controlled by the state on the data pad (140). As another variation, the first transistor (180) can be controlled by a second flip-flop (190) as so forth down the chain. These two different approaches provide an engineering tradeoff. As shown in FIG. 1, the system uses one fewer clock cycle to load the chain of flip-flops (190) and the corresponding transistors (180). However, this implies maintaining the state of the data pad (150) during operation. In contrast, adding an additional flip-flop (190) lengthens the load time by a clock cycle but makes the system independent of the data pad (150) state during operation. Either approach can be taken with the examples in this specification. Which approach is preferable will depend on the relative design value of data pad (150) state independence vs. loading time.

Figure 2:
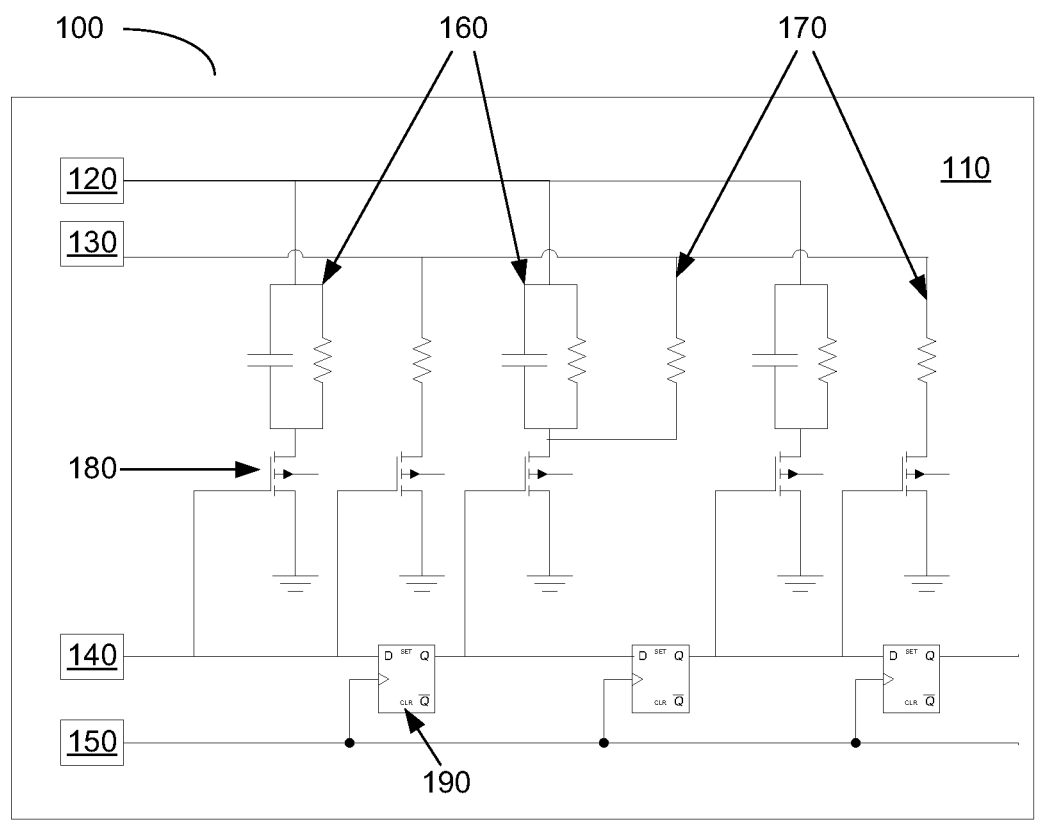
FIG. 2 shows an example system consistent with this specification.

FIG. 2 shows a system consistent with this specification. The system (100) comprises a substrate (110) with a plurality of sensors (160) and pumps (170). The substrate also has pad (120, 130, 140, 150) to facilitate communication with other devices. The first external communication pad (120) allows control signals to be provided to a pump (170). The second external communication pad (130) allows measurements to be obtained from a sensor (160). The data pad (140) and signal pad (150) are used to provide a serial series of bits to a series of flip-flops (190). The flip-flops (190) in turn control the transistors (180) which in turn determine which pump (170) and/or sensor (160) can be accessed using the external communication pads (120, 130).

FIG. 2 differs from FIG. 1 in that instead of providing independent flip-flops (190) and transistors (180) for each pump (170) and each sensor (160), a flip-flop (190) is associated with both a pump (170) and a sensor (160). In some versions, independent transistors are still provided for each pump (170) and sensor (160). In others, the transistors (180) are similarly combined for the paired sensor (160) and pump (170). Examples of both configurations are shown in FIG. 2. FIG. 2 shows all the pumps and sensors in paired configuration. However, other configurations are possible. For example, sensors that are used with just a particular pump may be arranged in this paired arrangement while other pumps and sensors may be arranged as shown in FIG. 1.

The approach shown in FIG. 2 has the advantage of reducing the propagation time for the flip-flops (190) and switching time between pumps (170) and sensors (160). In some examples, it may allow for more pumps (170) or sensors (160) to fit on a given substrate. It is also possible that a more general design such as shown in FIG. 1 can be converted to FIG. 2 after fabrication. One way this is performed is to arrange for some of the electrical connections to be severed. This can be done mechanically. This can also be done by including resistive elements as preset points and then melting the connections at the resistive elements by applying a high frequency current. When the conductor melts, surface tension causes the melted material to form a droplet, severing the conductive path. The material then cools and solidifies. Other methods exist to modify MEMS and electronic components post production, including laser, chemical, and thermal modifications. Post-production modification can reduce manufacturing and in some cases inventory costs using economies of scale. In one example, the system is provided in the general configuration and is modified at the point of use.

Although the pumps (170) are shown in a one to one configuration with the sensors (160), other configurations are possible within the scope of this specification. For example, multiple pumps (170) may be associated with a single sensor (160). Alternately, a pump (170) may be used with two different sensors (160). In one example, the pump (170) receives a first activation signal when a first sensor (160) is selected and the pump (170) receives a second activation signal when a second sensor (160) is selected. In some examples, the pump (170) receives multiple kinds of activation signals when a first sensor (160) is selected.

Figure 3:
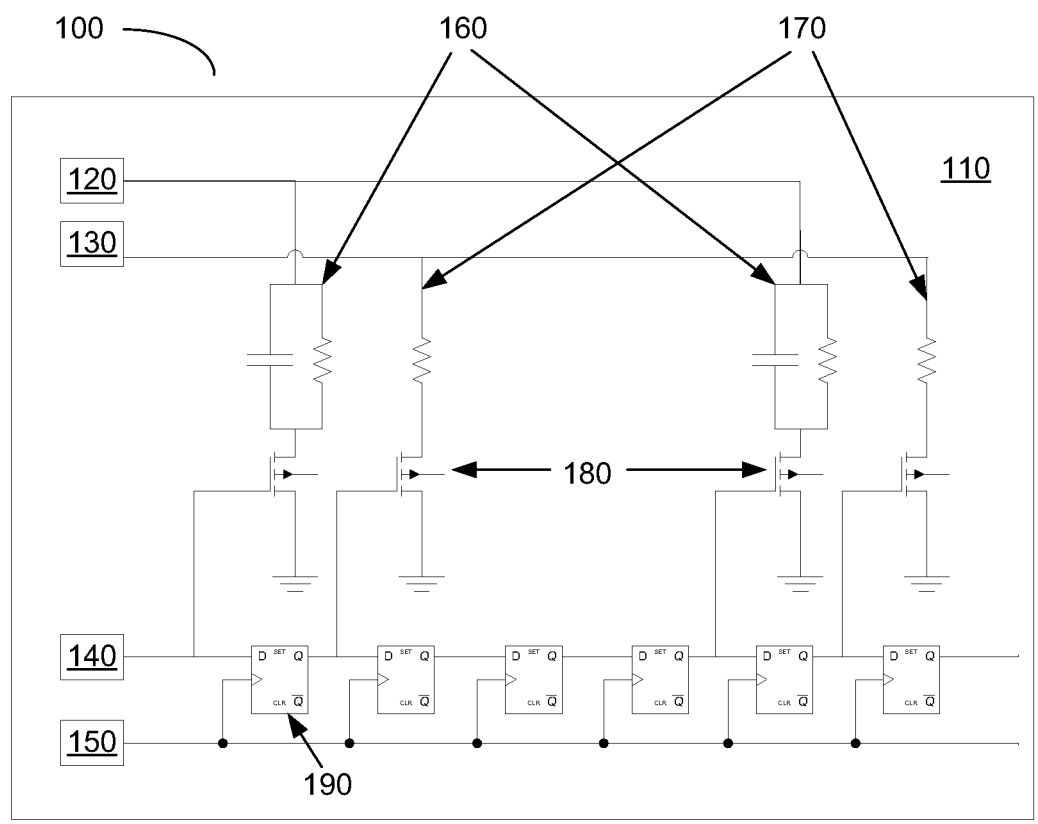
FIG. 3 shows an example system consistent with this specification.

FIG. 3 shows a system consistent with this specification. The system (100) comprises a substrate (110) with a plurality of sensors (160) and pumps (170). The substrate also has pad (120, 130, 140, 150) to facilitate communication with other devices. The first external communication pad (120) allows control signals to be provided to a pump (170). The second external communication pad (130) allows measurements to be obtained from a sensor (160). The data pad (140) and signal pad (150) are used to provide a serial series of bits to a series of flip-flops (190). The flip-flops (190) control the transistors (180) which in turn determine which pump (170) and/or sensor (160) can be accessed using the external communication pads (120, 130).

FIG. 3 differs from FIGS. 1 and 2 in that FIG. 3 includes flip-flops (190) in the chain of flip-flops (190) that are not connected to any transistor (180) and therefore do not allow selection of any pump (170) or sensor (160). These unconnected flip-flops (190) increase the overall propagation time for series of flip-flops (190). However, careful placement of these unconnected flip-flops (190) can reduce the switching time between a first configuration and a second configuration. The unconnected flip-flops (190) serve as storage locations for bits in the series of flip-flop (190). With proper placement, they can enable switching between two pumps and/or sensors that are separated by intervening pumps (170) and/or sensors (160) with a single signal to the signal pad (150). The signal results in the bits associated with the selected pump (170) and/or sensor (160) being advanced to an unconnected flip-flop (190) removing the previously selected pump (170) and/or sensor (160) from electrical connection with the external communication pads (120, 130). Further down the series of flip-flops (190), other bits are moved from an unconnected flip-flop (190) to a flip-flop (190) connected to a transistor (180). This allows signals to pass to and be obtained from the pump and/or sensor associated with the transistor (180).

Figure 4:
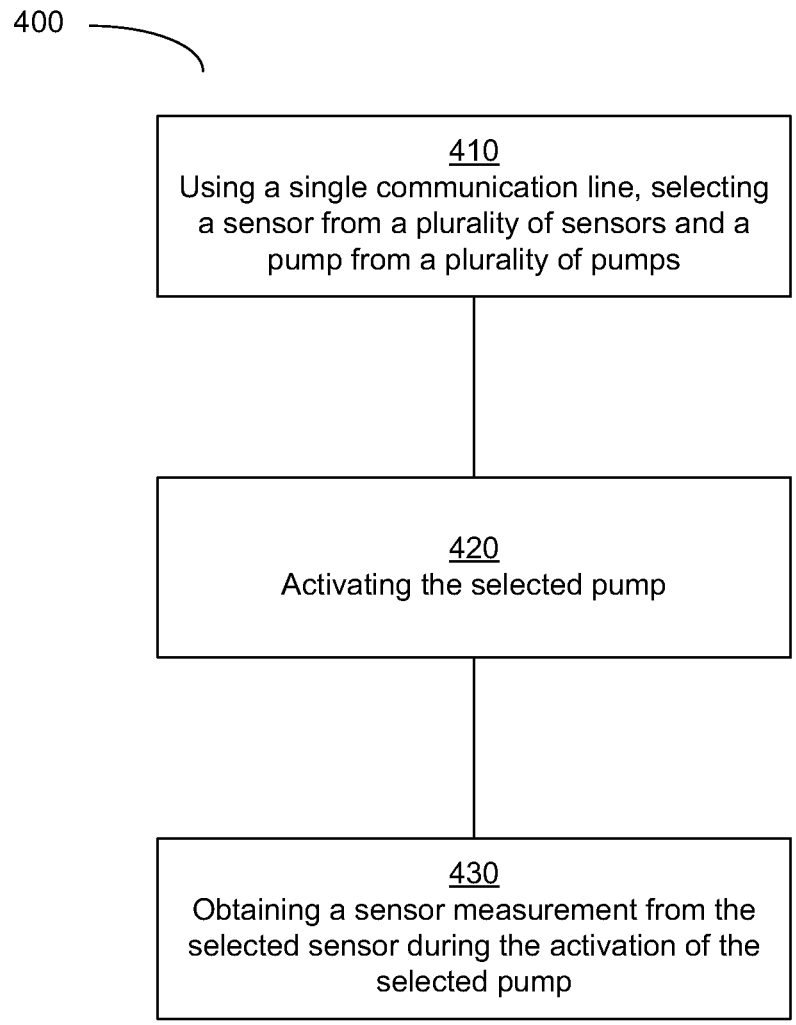
FIG. 4 shows an example method consistent with this specification.

FIG. 4 shows a method consistent with this specification. The method (400) using a single communication line, selecting a sensor from a plurality of sensors (160) and a pump from a plurality of pumps (170) (410); activating the selected pump (170) (420); and obtaining a sensor measurement from the selected sensor (160) during the activation of the selected pump (170) (430).

Operation (410) comprises using a single communication line, selecting a sensor from a plurality of sensors and a pump from a plurality of pumps. Using a single line reduces the cost of the test component by reducing the number of pads required. It also facilities using a variety of different test systems (100) with a given device because the device can use the two pads to control any number of pumps (170) and/or sensors (160). In contrast, if parallel loading were used, the number of potential selectable devices in the system depends on the number of pads/channels allocated for selection. Selection can be accomplished by serially providing selection bits that control the connection between the pumps and a pump line and the sensors and a sensor line.

Operation (420) comprises activating the selected pump. The selection transistors (180) allow the pump activation signal to activate just the selected pump (170) or pumps (170). This allows a single pump activation signal generator to provide all the pump activation signals to all the pumps (170) in the system (100) by changing which pump (170) is currently selected. This reduces the hardware needed in an associated device to interface with the system (100) since it can use a single generator rather than multiple generators.

Operation (430) comprises obtaining a sensor measurement from the selected sensor during the activation of the selected pump. This allows a single set of signal receiving and/or analysis hardware to be used with all the sensors (160) in the system (100). This can reduce the costs of a device used with the system (100) since a single piece of measurement equipment can be used for all sensors (160) of a given type in the system (100). This may also reduce the time to perform calibration on the device as the one piece of measurement equipment is used for multiple sensors (160). If the device uses an analog to digital converter, it similarly can be used with all of the sensors (160) again reducing the potential component costs for an associated device.

Figure 5:
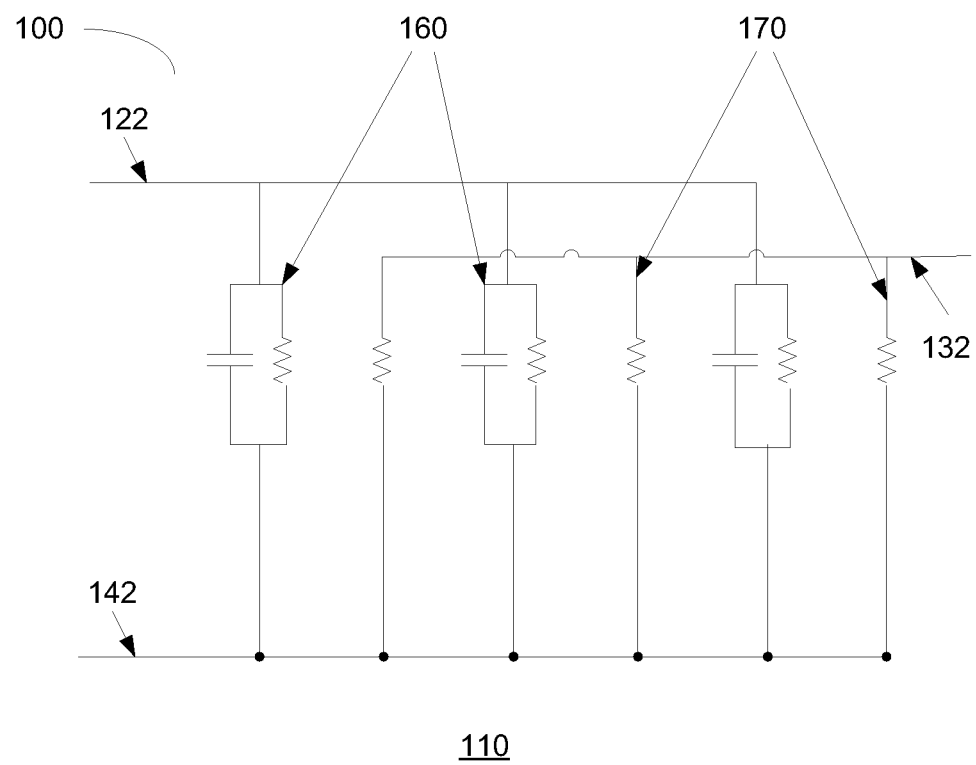
FIG. 5 shows an example system consistent with this specification.

Because the pump signal and sensor measurements are provided on different external communication pads (120, 130), operations 420 and 430 can be performed simultaneously. The use of separate external communication pads (120, 130) also reduces the noise from the pump activation signal on the sensor measurements. The use of different lines for the pump activation FIG. 5 shows a system consistent with this specification. The system (100) is a microfluidics system (100) on a substrate (110) with a plurality of pumps (170) and a plurality of sensors (160). The system includes a first communication line (142) for selecting a pump from the plurality of pumps (170) and selecting a sensor from the plurality of sensors (160); a second communication line (122) for providing an activation signal to the selected pump; and a third communication line (132) for obtaining an output from the selected sensor.

The first communication line is a data line (142) for selecting a pump from the plurality of pumps (170) and selecting a sensor from the plurality of sensors (160). The second communication line is a pump activation line (122) for activating the selected pump and not activating the non-selected pumps. The third communication line is a sensor line (132) to provide a sensor measurement from the selected sensor.

Within the principles described by this specification, a vast number of variations exist and that the examples are intended to be merely representative, without limiting the scope, applicability, or construction of the claims.

What is claimed is:

1. A microfluidics system, the system comprising:
   a plurality of pumps and a plurality of sensors;
   a first communication line connected to a plurality of transistors, the transistors connected to selectively enable operation of a selected pump from the plurality of pumps and a selected sensor from the plurality of sensor in response to a signal on the first communication line;
   a second communication line with branches that connect to each pump in the plurality of pumps such that a signal on the second communication line operates the selected pump selectively enabled by the plurality of transistors; and
   a third communication line with branches that connect to each sensor in the plurality of sensors such that output from whichever sensor is the selected sensor enabled by the plurality of transistors is transmitted on the third communication line.

2. The system of claim 1, further comprising a plurality of flip-flops connected to the plurality of transistors, wherein, upon receipt of a clock signal, the plurality of flip-flops transfers a state of a first transistor to a next transistor in the plurality of transistors.

3. The system of claim 1, wherein a first, single transistor of the plurality of transistors is connected to both a first pump of the plurality of pumps and a first sensor of the plurality of sensors so as to selectively enable both the first pump and the first sensor based on a state of the first transistor.

4. The system of claim 2, further comprising a greater number of flip-flops in the plurality of flip-flops than transistors in the plurality of transistors.

5. The system of claim 1, wherein the plurality of transistors is arranged to, in response to a selection signal, simultaneously enable multiple pumps from the plurality of pumps.

6. The system of claim 2, wherein each transistor in the plurality of transistors has a gate connected to a different flip-flop in the plurality of flip-flops.

7. The system of claim 1, further comprising:
   a substrate;
   the plurality of transistors and a plurality of flip-flops mounted on the substrate, the flip-flops arranged as a series;
   the plurality of pumps mounted on the substrate, each pump having an associated transistor, wherein a state of an associated transistor controls whether a corresponding pump is selected;
   the plurality of sensors mounted on the substrate, each sensor having an associated transistor, wherein a state of an associated transistor determines whether a corresponding sensor is selected;
   wherein each transistor of the plurality of transistors has an associated flip-flip that controls a state of a corresponding transistor;
   a data line providing a state to a first flip-flop in the series of flip-flops; and
   the first communication line comprising a signal line to provide a signal to the series of flip-flops, upon receipt of the signal on the signal line, a state of a flip-flop in the series of flip-flops is transmitted to a next flip-flop in the series of flip-flops.

8. The system of claim 7, wherein the plurality of pumps comprises at least four pumps.

9. The system of claim 8, wherein a number of the flip-flops exceeds a number of the transistors.

10. The system of claim 1, wherein the second communication line terminates in a single connection pad for receiving a signal to drive the selected pump.

11. The system of claim 1, wherein the third communication line terminates in a single connection pad for outputting a signal from the selected sensor.

12. The system of claim 1, wherein:
   each transistor is connected to a flip-flop; and
   the first communication line is connected to deliver a clock signal to each of the flip-flops.

13. The system of claim 1, wherein each transistor is connected between either a pump or a sensor and ground so as to selectively enable the connected pump or sensor with an electrical connection to ground.

14. The system of claim 1, the plurality of transistors arranged to enable the selected pump at a same time as the selected sensor.

* * * * *